United States Patent
Kim et al.

(10) Patent No.: US 9,610,312 B2
(45) Date of Patent: Apr. 4, 2017

(54) PAECILOMYCES VARIOTII VAR. BRUNNEOLUS GPP1101B, AND PREPARATION USING SAME

(71) Applicant: JS BIO CO., Ltd., Jeollabuk-do (KR)

(72) Inventors: Jong-Seog Kim, Jeollabuk-do (KR); Wang-hyu Lee, Jeollabuk-do (KR)

(73) Assignee: JS Bio Co., Ltd., Jeollabuk-Do (KR)

( * ) Notice: Subject to any disclaimer, the term of this patent is extended or adjusted under 35 U.S.C. 154(b) by 0 days.

(21) Appl. No.: 14/426,548

(22) PCT Filed: Sep. 2, 2013

(86) PCT No.: PCT/KR2013/007897
§ 371 (c)(1),
(2) Date: Mar. 6, 2015

(87) PCT Pub. No.: WO2014/038822
PCT Pub. Date: Mar. 13, 2014

(65) Prior Publication Data
US 2015/0224156 A1    Aug. 13, 2015

(30) Foreign Application Priority Data
Sep. 6, 2012 (KR) .......................... 10-2012-0098759

(51) Int. Cl.
*C12N 1/20*     (2006.01)
*A61K 36/258*   (2006.01)
*C12N 1/14*     (2006.01)
*C12R 1/79*     (2006.01)
*C12P 1/02*     (2006.01)

(52) U.S. Cl.
CPC .............. *A61K 36/258* (2013.01); *C12N 1/14* (2013.01); *C12P 1/02* (2013.01); *C12R 1/79* (2013.01)

(58) Field of Classification Search
None
See application file for complete search history.

(56) References Cited

FOREIGN PATENT DOCUMENTS

| KR | 1020110098122 | 9/2001 |
| KR | 1020030035708 | 9/2003 |
| KR | 10200900835   | 8/2009 |
| KR | 1020100116562 | 11/2010 |

OTHER PUBLICATIONS

Xu et al (Phytomedicine : international journal of phytotherapy and phytopharmacology, (Jun. 2009) vol. 16, No. 6-7, pp. 609-616.*
Kwak, Y., et al., "Identification and Thermal Resistance of *Penicillium* sp. Isolated from Korean Ginseng," Korean Journal of Ginseng Science, Jun. 1993, pp. 148-152, vol. 17, No. 2.
Extended Supplementary European Search Report dated Mar. 31, 2016, received for European Application No. 13835795.9.
Yan, Q., et al., "Purification Method Improvement and Characterization of a Novel Ginsenoside-Hydrolyzing β-Glucosidase from Paecilomyces Bainier sp. 229", Bioscience, Biotechnology, and Biochemistry, Feb. 7, 2008, pp. 352-359, vol. 72, No. 2.
Choi, K., et al., "Research Trends of Fermented Medicinal Herbs-Based on Their Clinical Efficacy and Safety Assessment", Journal of Life Science, Dec. 6, 2012, pp. 1729-1739, vol. 22, No. 12.
Zhou, W., et al., "Biotransformation of Panax notoginseng saponins into ginsenoside compound K production by Paecilomyces Bainier sp. 229", Journal of Applied Microbiology, Mar. 2008, pp. 699, 706, vol. 104, No. 3.

* cited by examiner

*Primary Examiner* — Jennifer Graser
(74) *Attorney, Agent, or Firm* — Fleit Gibbons Gutman Bongini Bianco PL; Jose Gutman (57) ABSTRACT

The present invention relates to a *paecilomyces variotii* var. *brunneolus* GPP1101B (microorganism deposit number KCTC 119938BP) isolated during a *ginseng* fermentation process, and a preparation using the same. According to the present invention, remarkable anticancer, immune regulation, mutation inhibition and antibacterial effects are obtained by injecting the strain or the preparation into a *ginseng* extract or into a red *ginseng* extract.

19 Claims, 10 Drawing Sheets

PAECILOMYCES VARIOTII VAR. BRUNNEOLUS GPP1101B, AND PREPARATION USING SAME

TECHNICAL FIELD

The present invention relates to a *paecilomyces variotii* var. *brunneolus* GPP1101B strain and preparation using the same, and in particular to a *paecilomyces variotii* var. *brunneolus* GPP1101B strain which have remarkable anti-cancer, immune regulation, mutation inhibition and antibacterial effects by injecting a *ginseng* extract or a red *ginseng* extract, and preparation using the same.

BACKGROUND ART

In general, *ginseng* is a medicinal plant generally used for the sake of anti-fatigue, anti-stress, immune function enhancement, and blood sugar drop, saponin is recognized as a key component of such effects.

In addition to the saponin component of the *ginseng*, researches are being conducted on the processing technology of *ginseng* so as to enhance the effects. So, many trials are under way to find out any one of saponin components which have not been found in common raw *ginseng* and dry *ginseng* and to prove the effects through such findings.

As a technology for improving the effects with respect to the conventional *ginseng*, the Korean patent publication registration number 10-0144130 disclose "*ginseng* protein-bound polysaccharides ("Jinsan"), which contains 40.0~50.0% of hexose consisting of glucose and galactose, 41.0~44.8 of galacturonic acid which is acidic sugar and 3.7~5.2% of protein consisting of lysin, histidine, arginine, aspartic acid, threonine, serine, glutamic acid, proline, glycine, alanine, valine, methionine, isoleucine, leucine, tyrosine, cysteine and phenylalanine and has molecular weight of 50,000~150,000 and is directed to polysaccharides which shows an effect of improving immunity.

In addition, the Korean Patent Registration No. 10-0361187 discloses "*ginseng paecilomyces* with good blood making promotion operation, bone marrow protection operation, cancer cell immune cell creation operation and radiation sensitivity operation", which is characterized in that *ginseng* root powder is extracted using methanol, and methanol insoluble residue is dried in the shade, and water soluble fraction obtained by extracting using distilled water is frozen and dried, and ethanol insoluble fraction is obtained by adding ethanol to the thusly obtained substance, and the ethanol insoluble fraction is processed through dialysis, thus obtaining *paecilomyces*, and six fractions are obtained by sephacryl S-500 column chromatography, and purely separated and refined *ginseng paecilomyces* is obtained by performing DEAE-cellulose column chromatography with respect to each of the six fractions, thus producing *paecilomyces* which has good blood making promotion operation, bone marrow protection operation, cancer cell killing immune cell creation operation and radiation sensitivity operation.

However, the above-described conventional technology has a limited use range, and refining efficiency is not high, and there is a limit in obtaining a predetermined effect. Therefore, it needs to develop a new concept of immune active agent which uses *ginseng* and has good efficiency.

SUMMARY OF THE INVENTION

Technical Problem

Accordingly, the present invention is made in an effort to resolve the problems in the conventional art. It is an object of the present invention to provide a good anticancer and immune regulation effect and a mutation inhibition and antibacterial active agent effect by adding *ginseng* extract or red *ginseng* extract.

Other objects of the present invention may be well understood along the description below with respect to the exemplary embodiments.

Solution to Problem

To achieve the above objects, there is provided a strain of *paecilomyces variotii* var. *brunneolus* GPP1101B (microorganism deposit number KCTC 11993BP) which is isolated during a *ginseng* fermentation process.

According to another aspect of the present invention, there is provided an immune active agent, which may include a culture liquid cultivated by inputting into an extract liquid of *ginseng* or red *ginseng* a strain of *paecilomyces variotii* var. *brunneolus* GPP1101B (microorganism deposit number KCTC 11993BP).

In the immune active agent, the culture liquid may be a culture filtrate which is obtained by filtering over grown strain.

In the immune active agent, the culture liquid may be frozen and dried and included.

According to further another aspect of the present invention, there is provided an antibacterial active agent, which may include a culture liquid cultivated by inputting into an extract liquid of *ginseng* or red *ginseng* a strain of *paecilomyces variotii* var. *brunneolus* GPP1101B (microorganism deposit number KCTC 11993BP).

In the antibacterial active agent, the culture liquid may be a culture filtrate which is obtained by filtering over grown strain.

In the antibacterial active agent, the culture liquid may be frozen and dried and included.

According to still further another aspect of the present invention, there is provided an antitumor agent, which may include a culture liquid cultivated by inputting into an extract liquid of *ginseng* or red *ginseng* a strain of *paecilomyces variotii* var. *brunneolus* GPP1101B (microorganism deposit number KCTC 11993BP).

In the antitumor agent, the culture liquid may be a culture filtrate which is obtained by filtering over grown strain.

In the antitumor agent, the culture liquid may be frozen and dried and included.

According to still further another aspect of the present invention, there is provided an anti-mutagen, which may include a culture liquid cultivated by inputting into an extract liquid of *ginseng* or red *ginseng* a strain of *paecilomyces variotii* var. *brunneolus* GPP1101B (microorganism deposit number KCTC 11993BP).

In the anti-mutagen, the culture liquid may be a culture filtrate which is obtained by filtering over grown strain.

In the ant-mutagen, the culture liquid may be frozen and dried and included.

According to still further another aspect of the present invention, there is provided a method for manufacturing a culture liquid, which may include cultivating the culture liquid by inputting into an extract liquid of *ginseng* or red *ginseng* a strain of *paecilomyces variotii* var. *brunneolus* GPP1101B (microorganism deposit number KCTC 11993BP).

In the method for manufacturing a culture liquid, the extract liquid of *ginseng* or red *ginseng* may be a solution obtained by inputting *ginseng* or red *ginseng* into water and heating for 12~72 hours at a temperature of 60~100° C. and filtering the *ginseng* or the red *ginseng*.

According to the method for manufacturing a culture liquid, in the cultivation, the extraction liquid of *ginseng* or red *ginseng* into which the strain is contained may be cultivated for 10~60 days at a temperature of 15~35° C. using a cultivator.

In the method for manufacturing a culture liquid, after the cultivation is finished, the over grown stain may be filtered and used to manufacture a culture filtrate.

Advantageous Effects

According to the *paecilomyces variotii* var. *brunneolus* GPP1101B strain and preparation using the same, and in particular to a *Paecilomyces variotii* var. *brunneolus* GPP1101B strain and preparation using the same, it is possible to obtain remarkable anticancer, immune regulation, mutation inhibition and antibacterial effects by injecting a *ginseng* extract or a red *ginseng* extract.

DETAILED DESCRIPTION

The present invention may be modified into various forms and may have various exemplary embodiments. Specific exemplary embodiments are shown in the drawings, and the present invention will be described, which are not intended to limit specific exemplary embodiments of the present invention. It should be understood that the present invention includes all changes, equivalents or alternatives which belong to the technical concept and range of the present invention, and the present invention may be modified into various types. The scope of the present invention is not limited by the following exemplary embodiments.

The exemplary embodiments of the present invention will be described with reference to the accompanying drawings. Irrespective of the reference numbers in the drawings, the same or corresponding components are given the same reference numbers. The repeating descriptions may be omitted.

The strain of *paecilomyces variotii* var. *brunneolus* GPP1101B (microorganism deposit number KCTC 11993BP) which proves to have remarkable antibacterial and immune activity is isolated during a *ginseng* fermentation process, thus providing remarkable antibacterial and immune activity.

Yellow unique filamentous fungi was collected from the fermentation tank of *ginseng*, and the isolated strain was cultivated at a predetermined culture medium, and the cultivated strain was isolated, and the homology with other bacteria which had been reported before was measured, and the isolated strain was identified. As a result, the isolated strain GPP1101B was proved to be *paecilomyces variotii* var. *brunneolus* GPP1101B strain.

It is possible to manufacture an immune active agent such as a food composition, etc. wherein the strain of the GPP1101B is contained as an effective component. Such an immune active agent may be manufactured during the process wherein the strain of the GPP1101B is cultivated in *ginseng* fermentation liquid, and the cultural liquid is extracted and frozen and dried. Here, the culture of such a strain may be performed in an aerobic state of 10~30° C.

In addition, it is possible to manufacture the preparation such as immune active agent, antibacterial active agent, anticancer and antimutagenic agent, etc. which contains the liquid cultivated by injecting the strain of the GPP1101B, namely, *paecilomyces variotii* var. *brunneolus* GPP1101B (microorganism deposit number KCTC 11993BP) into the extract liquid of *ginseng* or red *ginseng*. Such preparation has features in that the liquid itself cultivated by injecting the strain of the GPP1101B into *ginseng* or red *ginseng* extract liquid has immune active agent, antibacterial active agent, anticancer and anti-mutation effects, etc. It may contain a part of or all or effective components. Medicinal materials may be contained or foods may be contained. Here, the cultivated liquid may be the filtrate after the cultivation, wherein the over grown strain of the GP1101B is filtered after the cultivation. It may be contained in the preparation after freezing and drying.

Meanwhile, the culture liquid contained in the preparation, for example, immune active agent, antibacterial active agent, anticancer and antimutagenic agent, etc. may be manufactured by injecting the strain of the GPP1101B into the *ginseng* or red *ginseng* extract liquid. Here, the extract liquid of *ginseng* or red *ginseng* may be the solution obtained in such a way that *ginseng* or red *ginseng* is input in water and is heated for 12~72 hours at a temperature of 60~100° C. in an extraction boiler, and the *ginseng* or red *ginseng* is filtered. Using the extraction liquid of *ginseng* or red *ginseng* into which the strain of the GPP1101B is inputted, the cultivation may be performed for 10~60 days at a temperature of 15~35 C using the extraction boiling of the cultivator. Meanwhile the culture liquid may be manufactured as a filtrate by filtering the strain of the over cultivated GPP111B after the cultivation is finished.

Embodiment 1

Isolation and Behavior of Strain

Yellow unique filamentous fungi was collected from the *ginseng* fermentation tank that a farmer uses and was observed using an optical microscope. It was input on a potato nutrient agar to which 200 ppm of streptomycin was added and was cultivated for 5 days at 25° C.

The yellow spore among the colony formed in the culture medium was formed a lot, and a single fungi was collected and was purely isolated as a GPP1101B strain.

The isolated strain was cultivated in the potato nutrient agar (200 g of potato, 15 g of agar, 15 g of dextrose, 1 liter of distilled water) which was most generally used in the experimental rooms, and when the strain was enough grown, the strain was kept in the refrigerator and was used for the experiment.

Figure 1:
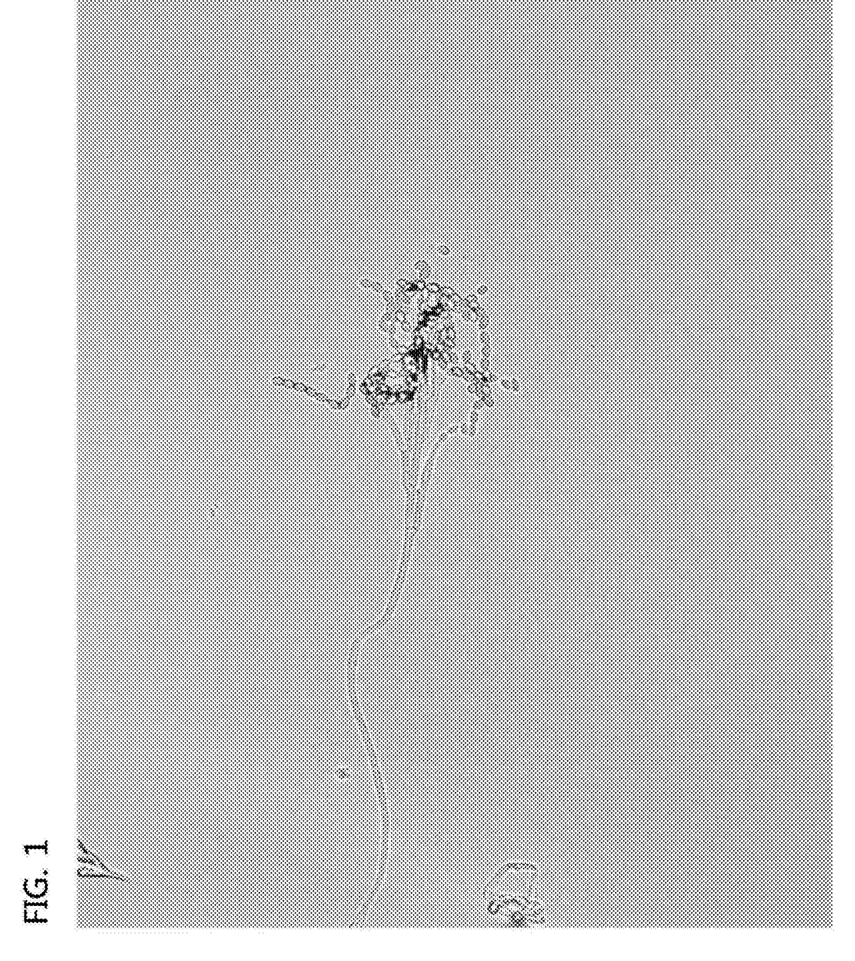
FIG. 1 is an image illustrating a conidiophore and conidium observed using an optical microscope of a strain according to the present invention.
Figure 2:
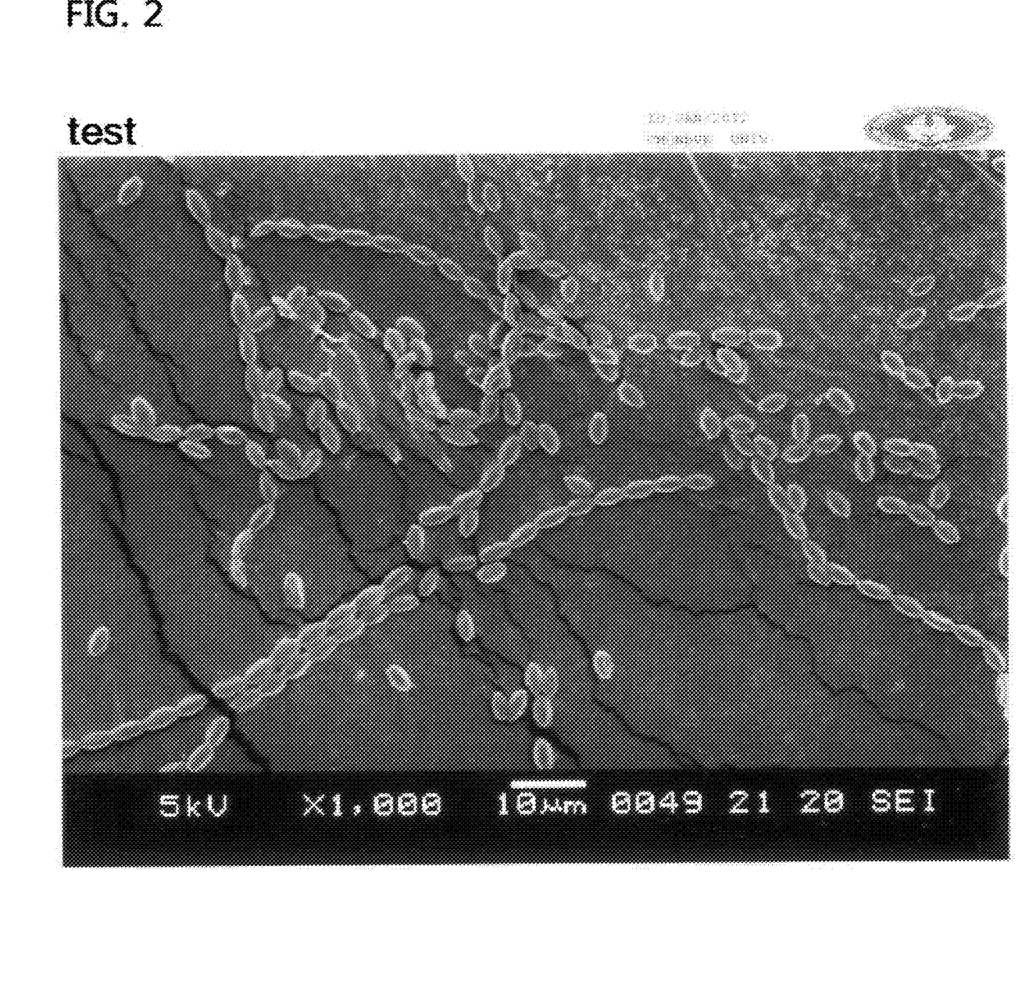
FIG. 2 is an image illustrating the type of a conidium observed using an electron microscope of a strain according to the present invention.
Figure 3:
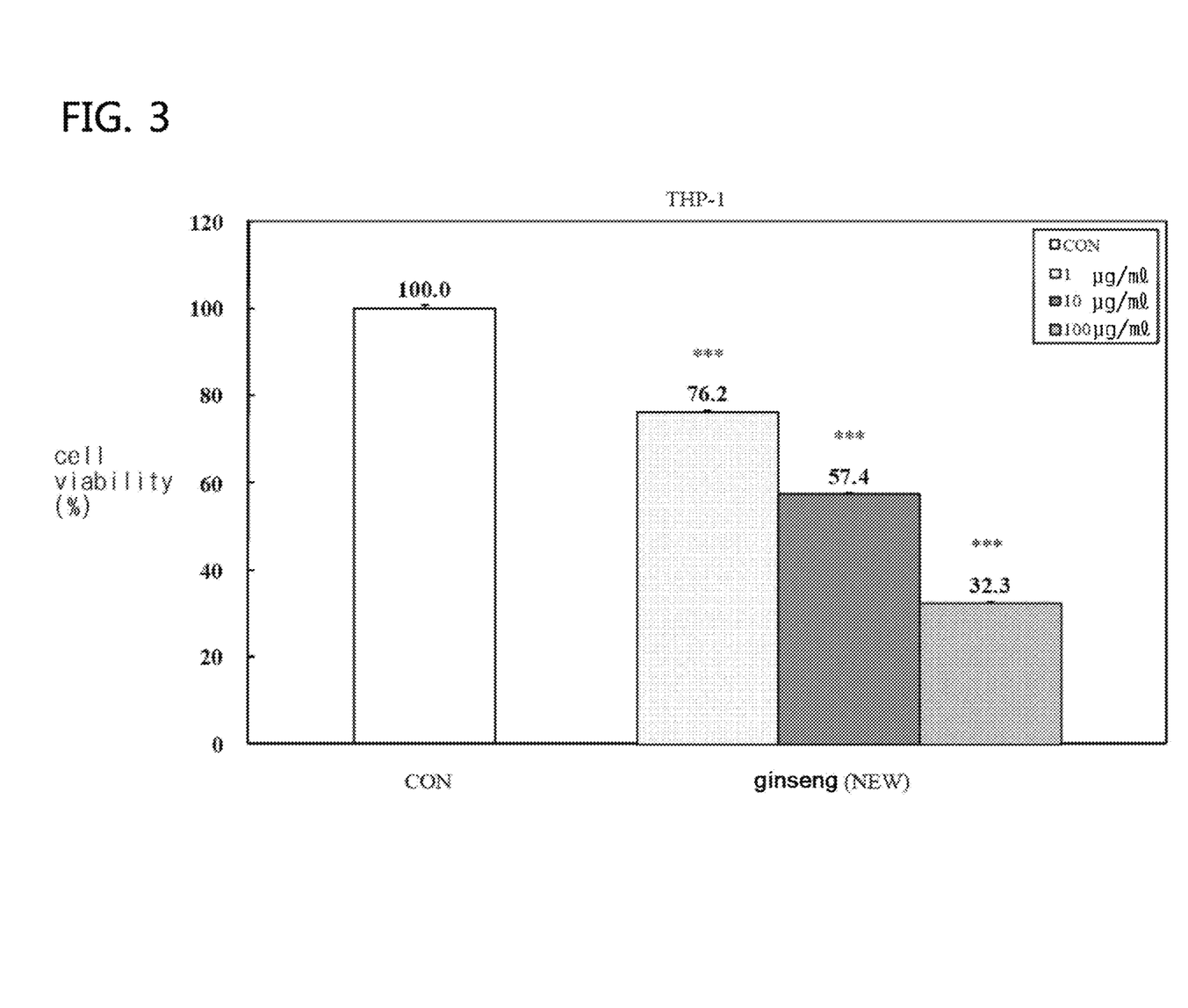
FIGS. 3 to 6 are graphs for describing a result of the experiment performed with respect to the anticancer characteristic of preparation according to the present invention.
Figure 4:
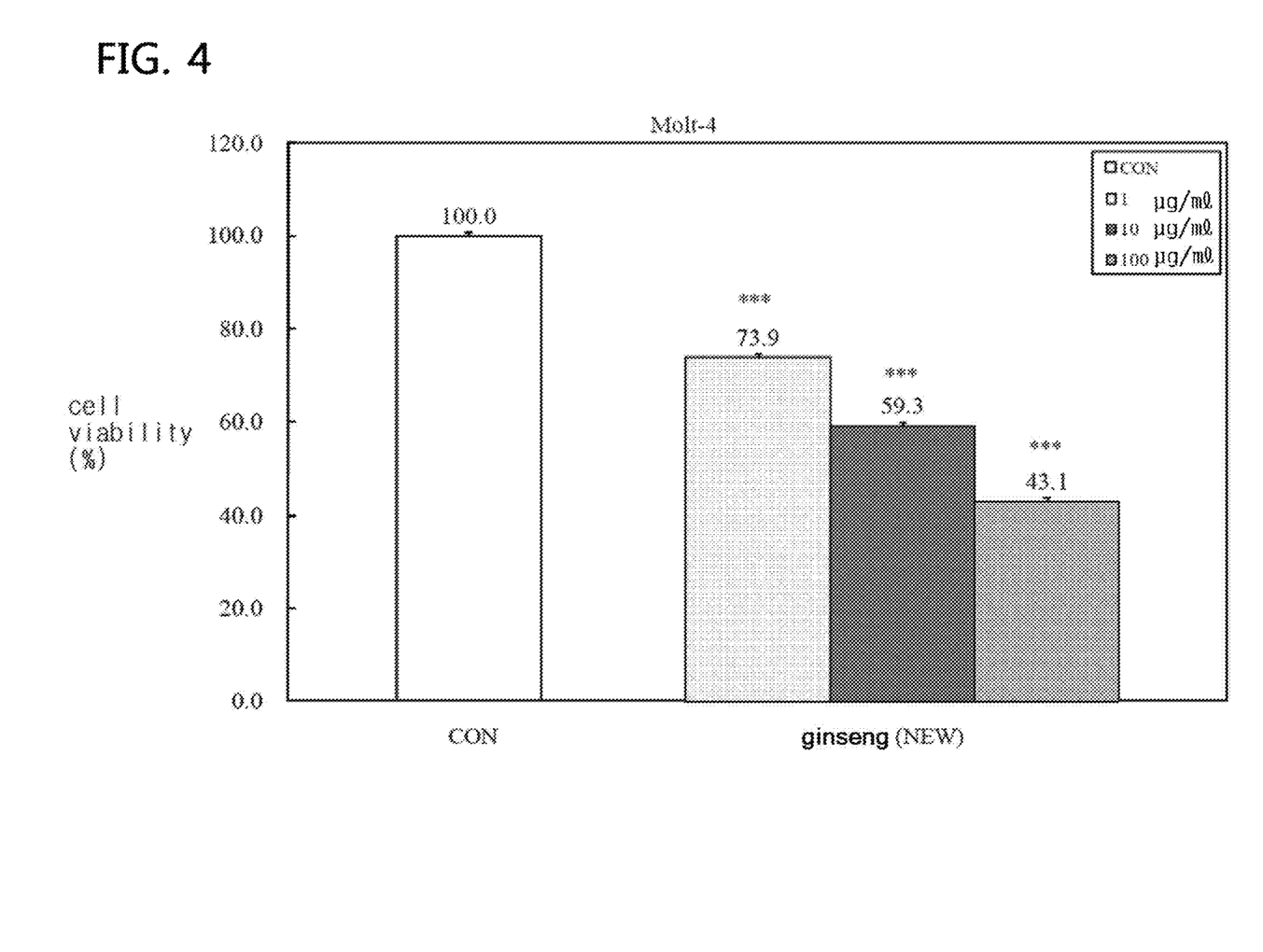
Figure 5:
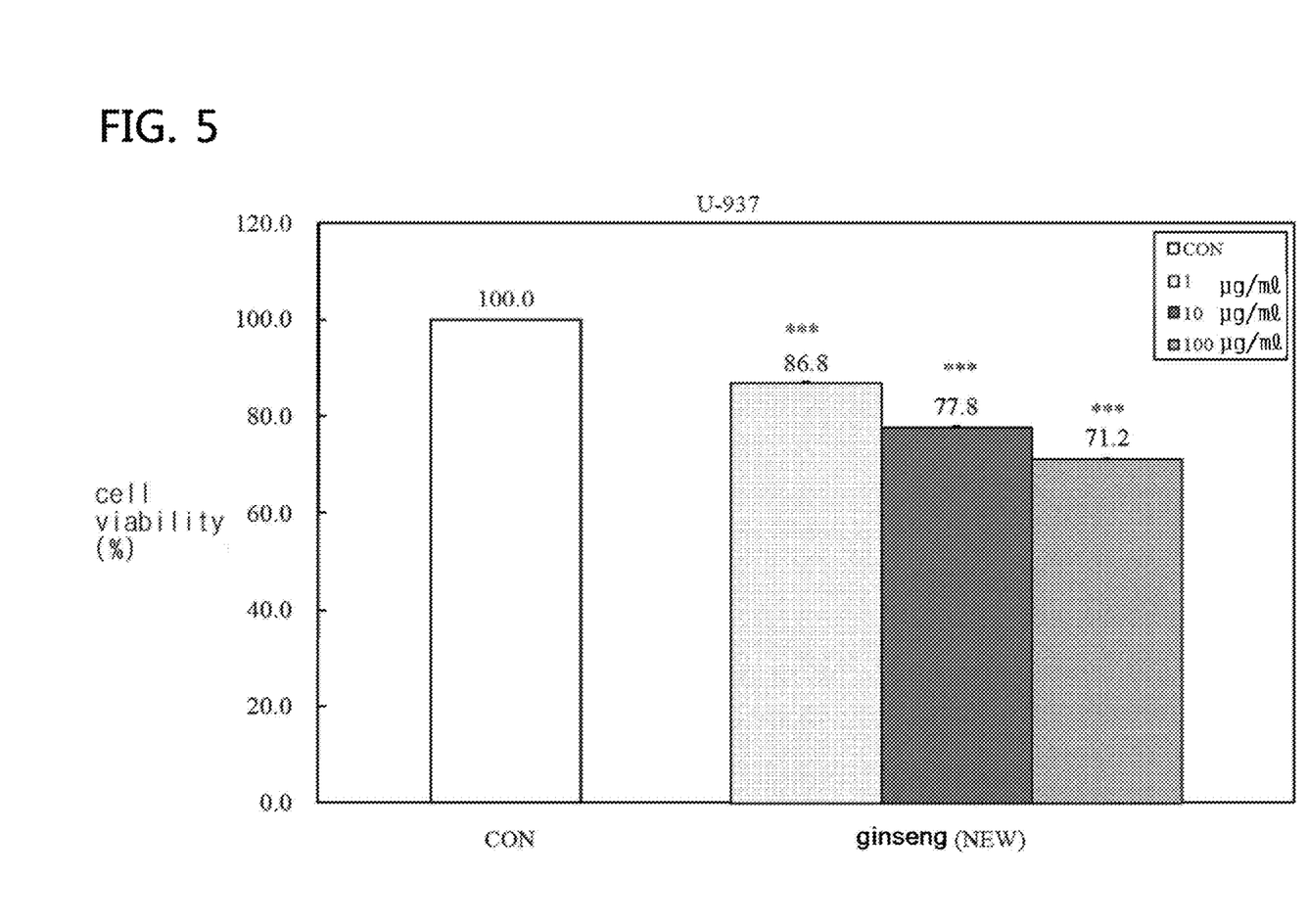
Figure 6:
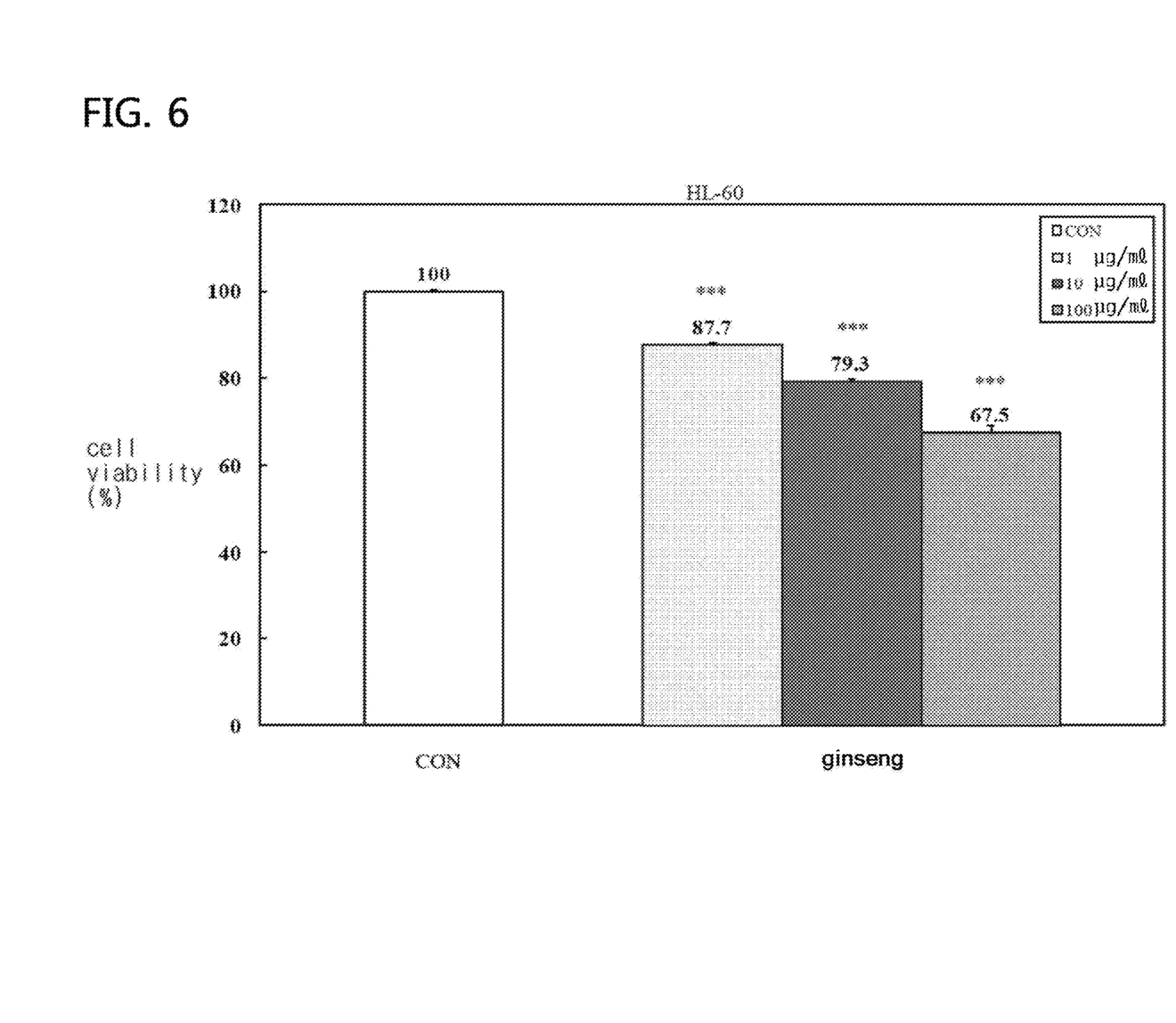

Since the GPP1101B had a feature where it may well grew in any culture medium, it was proved that the GPP1101B well grew in a byproduct. As seen in the image taken using the optical microscope in FIG. 1, the conidiosphore had a simple appearance and was not easily branched. In addition, as seen in the image taken using the optical microscope in FIG. 2, the spore was a single cell like a rice grain wherein the size of the spore was very small, namely, a few μm, while forming a conidium like a connection ring.

The GPP1101B grew well in the aerobic state of 10~30° C., in particular, the temperature of 20~26° C. was the optimum temperature for the growth of spawn, and the spawn and spore formation amount was increased faster in case of shake culture in the liquid culture medium rather than the flat plate culture medium. The spore was well formed at 10~30° C., and it was good at 5~26° C.

Different from the conventional *penicillium*, the GPP1101B had a longer chain in terms of various morphological characteristics, and the GPP1101 was identified to belong to *paecilomyces* group in terms of its morphology. The identification through the PCR was requested to Bynics Corporation, and it was identified as having 99% similarity. In this group, avirulence bacteria was present in various plants, and it was related to fungi which had caused diseases to insects. In addition, such a strain was proved to form an inhibition zone a result of the inoculation of *pseudomonas aeruginosa* and *staphylocossus aureus* after the strain was cultivated in the extraction liquid of *ginseng* or red *ginseng*, and the filtrate was extracted and frozen and dried and was added to a culture medium by a predetermined amount, and it was not effective against colon bacterium and *salmonella*. Since it was proved that the antibacterial active agent was lost when the sample with respect to the filtrate of the cultivation was processed (autoclave, 121° C., 15 minutes), such a substance seemed to be weak against the heat. In addition, it was proved that low antibacterial active agent was obtained with respect to fungi and *actinomyces*.

The GPP1101B was deposited to the microorganism resource center of the Korea Research Institute of Bioscience and Biotechnology (KCTC) as of Aug. 4, 2011, with the deposit number "KCTC11993BP". The following table 1 shows a result of the component analysis with respect to the samples of the conventional *ginseng* extraction solution (number 102) and the GPP1101B culture liquid (number 105) of the *ginseng* extraction solution requested to the Korean Food Research Institute (KFRI, reference number AO2012-02-01-028) as of Jan. 26, 2012.

TABLE 1

| Items | Result of analysis Number 102 | Result of analysis Number 105 | units | Test method UHPLC-UVD measuring method |
|---|---|---|---|---|
| Rg1 | 0.0 | 0.0 | mg/100 g | |
| Re | 0.0 | 0.0 | mg/100 g | |
| Rf | 14.4 | 158.7 | mg/100 g | |
| Rh1(S) | 40.4 | 283.8 | mg/100 g | |
| Rg2(S) | 25.6 | 150.6 | mg/100 g | |
| Rg2(R) | 36.8 | 204.0 | mg/100 g | |
| Rh1(R) | 53.7 | 328.3 | mg/100 g | |
| Rb1 | 0.0 | 0.0 | mg/100 g | |
| Rc | 0.0 | 0.0 | mg/100 g | |
| F1 | 0.0 | 0.0 | mg/100 g | |
| Rb2 | 0.0 | 33.8 | mg/100 g | |
| Rb3 | 0.0 | 0.0 | mg/100 g | |
| Rd | 0.0 | 29.9 | mg/100 g | |
| F2 | 269.8 | 509.0 | mg/100 g | |
| Rg3(S) | 103.5 | 568.1 | mg/100 g | |
| Rg3(R) | 40.4 | 179.3 | mg/100 g | |
| PPT[1](S) | 0.0 | 0.0 | mg/100 g | |
| PPT(R) | 0.0 | 0.0 | mg/100 g | |
| K[2] | 0.0 | 0.0 | mg/100 g | |
| Rh2(S) | 0.0 | 0.0 | mg/100 g | |
| Rh2(R) | 0.0 | 0.0 | mg/100 g | |
| PPD[3] | 0.0 | 0.0 | mg/100 g | |

PPT: Protopanaxatriol.
[2]K: Compound K.
[3]PPD: Protopanaxadiol.

As seen in Table 1, it is proved that the GPP1101B culture liquid (number 105) of *ginseng* extract liquid contains a lot of components as compared with the conventional *ginseng* extract liquid (number 102) in terms of Rf which shows the operation of pain inhibition and lipid peroxide inhibition, etc., Rh1 which shows injury inhibition operation between experiments, Rg2 which shows platelet cohesion inhibition, memory failing improvement, etc., Rb2 which shows sugar and fat metabolism promotion, anti-diabetic operation, etc., Rd which shows adrenal cortex stimulation hormone and corticosterone secretion promotion operation, and Rg3 which shows cancer cell transfer inhibition operation, injury inhibition operation between experiments.

Embodiment 2

Anticancer Characteristic

The anticancer characteristic on the sample using the GPP1101B was tested.

In order to measure the cell survival rate, $MTT_{assay}$ was used. The sample was 1~100 ug/Ml of *ginseng* culture liquid (KJS), and the passage cell line was THP-1 (human acute monocyticleukemia cell line), Molt-4 (human lymphoblastic leukemia), U-937 (human tissue profile leukemia cell line) and HL-60 (human acute promyelocytic leukemia cell line). In addition, the same was manufactured in such a way that the sample solution made by inputting water and *ginseng* or red *ginseng* in the extraction boiler and boiling for 12~72 hours at 60~100° C. was input in the incubator along with the GPP1101B strain and was cultivated for 10~60 days at 15~35° C. The above method was identically used to the samples embodiments 3 to 5) of another exemplary embodiments.

As for the experiment method, the sample with a concentration (0.1~10 ug/ml) was added to the leukemia cell culture medium such THP-1, etc. based on the MTT method, and the medium was cultivated in the $CO_2$ cultivator of 37° C. for 48 hours. 20 Ml of the MTT solution diluted in the DPBS-A (pH 7.4) was added to each well at a concentration of 5 mg/Ml 4 hours before the end of the cultivation, and it was resolved with 100 μl of SDS 10% melted in 0.1N HCL, and the light was blocked with a silver sheet or 18 hours. The absorbance of each well was measured at 570 cm using the ELISA leader and was compared with the control group, and the cell survival rate was calculated into percentage, and the calculated values are shown in FIGS. 3 to 6.

THP-1 (human acute monocyticleukemia cell line), Molt-4 (human lymphoblastic leukemia), U-937 (human tissue profile leukemia cell line) and HL-60 (human acute promyelocytic leukemia cell line) cells were passage-cultivated, and the *ginseng* culture liquid (KJS) of each concentration (0.1~10 ug/ml) was added, and the cell survival rate of the leukemia cell was checked. As illustrated in FIGS. 3 to 6, it was observed that in all the leukemia cell lines used in the experiments had anticancer activity which inhibited the concentration-dependent cell survival rate. In particular, the survival rate inhibition effects was remarkable in the THP-1 cell and the Molt-4 cell.

Embodiment 3

Immune Regulation Characteristic

The characteristics of the immune regulation with respect to the sample which uses the GPP1101B was tested.

The sample was orally administered 250 or 500 mg/kg B.W.) for 4 weeks to the BALB/c mouse so as to measure the lymphocyte (T, B cells) and a subpopulation, and spleen and thymus were taken out, thus manufacturing spleen and thymus cell-floated liquid. The 1×10$^6$ cell/well was double dyed using PE conjugated anti mouse B220 antibody and FITC conjugated anti-mouse Thy-1 antibody and was reacted for 30 minutes at 4°, and the subpopulation of the lymphocyte was measured using the flow cytometer (excitation: 488 nm, emission: 525 nm/FITC, 755 nm/PE.

In addition, in order to measure the blood cytokine (IFN-γ, IL-2, IL-4), the concentration of the IFN-γ in the blood serum was measured using the mouse IFN-γ ELISA Ready-Set-Go (eBioscience corporation).

The purified anti-mouse IFN-γ antibody was coated (100 ul/well) on the microplate (96 wells), and the adsorption was performed while blocking the light (overnight) at 4° C. Each well was aspirated and washed three times with a wash buffer (300 ul/well) and was diluted with an assay diluent buffer and was reacted for 1 hour at a room temperature. Each well was aspirated, and a clinical specimen and a standard solution (recombinant mouse IFN-γ, 1 ug/ml) was added by 100 μl for each well and was reacted for 2 hours at a room temperature and was washed three times, and a detection antibody diluted with an assay diluent (1×) was injected by 10 μl for each well and was reacted for 1 hour at a room temperature. Washing three times with a wash buffer (300 ul/well), an avidin-HRP antibody was added by 100 μl for each well and was reacted for 1 hour at a room temperature and was washed three times, and a substrate solution was added by 100 μl for each well and was colored for 15 minutes under light-blocked environment. The reaction was stopped by adding a stop solution, and the absorbance was measured at a wavelength of 450 nm using the ELISA reader. In addition, the measurement of IL-2 and IL-4 were performed based on the measurement method of IFN-γ.

Figure 7:
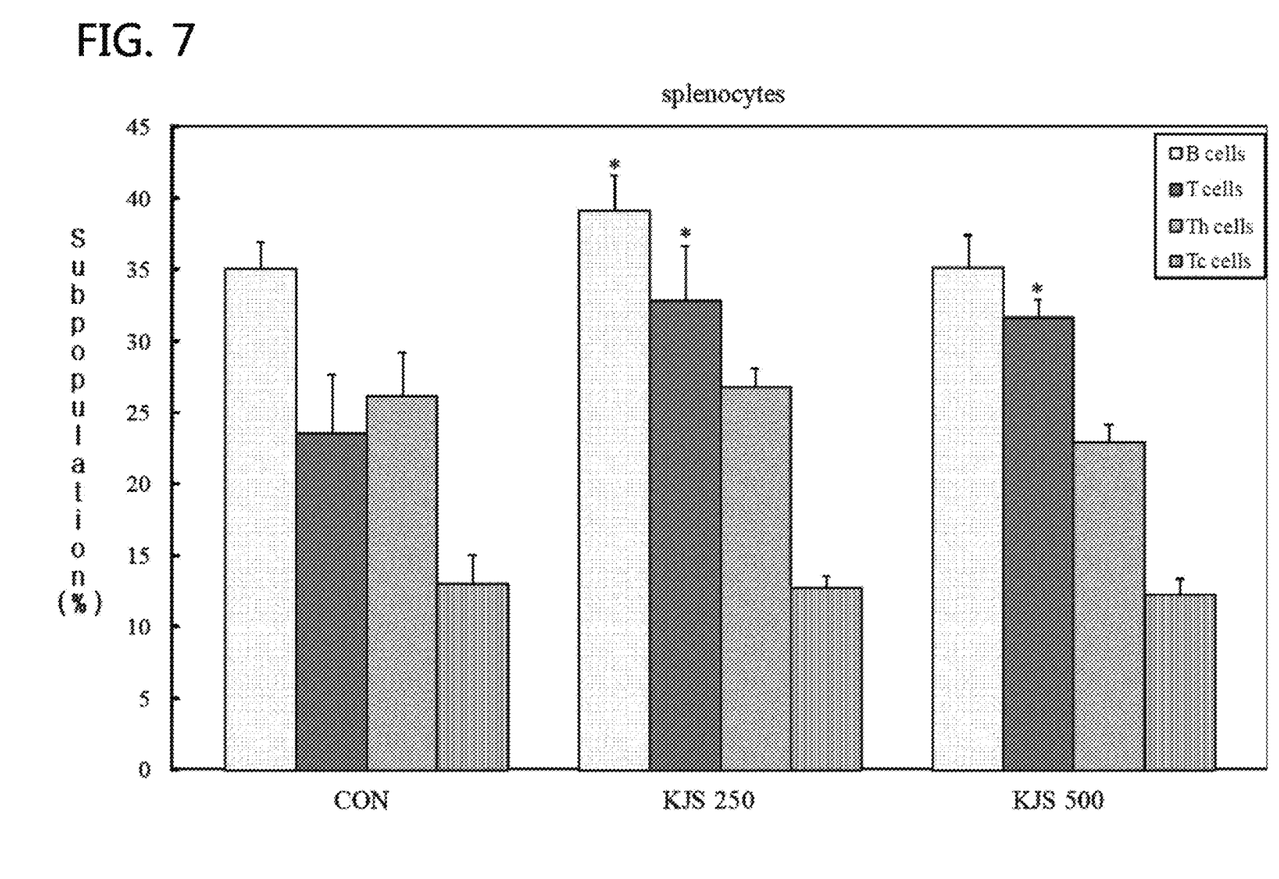
FIGS. 7 and 8 are graphs for describing a result of the experiment performed with respect to an immune regulation characteristic of preparation according to the present invention.

The effects to the spleen and thymus lymphocyte subpopulation are shown in Table 2 and FIG. 7.

TABLE 2

| | Lymphocyte subpopulation | | | | |
|---|---|---|---|---|---|
| | | Cell Type | | | |
| | Splenocytes (%) | | | Thymocytes (%) | |
| | | T cells | | | |
| Treat | B cells | $T_H$ | $T_C$ | $T_H$ | $T_C$ |
| CON | 35.0 ± 2.1 | 23.5 ± 4.2 | | 15.1 ± 0.3 | 11.2 ± 0.4 |
| | | 26.2 ± 3.1 | 13.0 ± 2.1 | | |
| KJS 250 | 39.1 ± 2.6* | 32.8 ± 3.9* | | 13.0 ± 0.6 | 8.9 ± 0.6 |
| | | 26.8 ± 1.4 | 12.8 ± 0.9 | | |
| KJS 500 | 35.1 ± 2.4 | 31.6 ± 1.3* | | 13.0 ± 0.6 | 10.0 ± 0.4 |
| | | 22.9 ± 1.3 | 12.3 ± 1.2 | | |

KJS 250: 250 mg/kg B.W. p.o.
KJS 500: 500 mg/kg B.W. p.o.
*Significantly different from control group (*p < 0.05).

The KJS sample was orally administrated for 4 weeks to the BALB/c mouse, and as a result of the spleen and thymus lymphocyte subpopulation, the numbers of the B-lymphocytes and the T-lymphocytes were increased in significance at the 20 mg/kg B.W administration concentration. Like this, it was proved that the *ginseng* culture liquid had regulated up the immune power.

Figure 8:
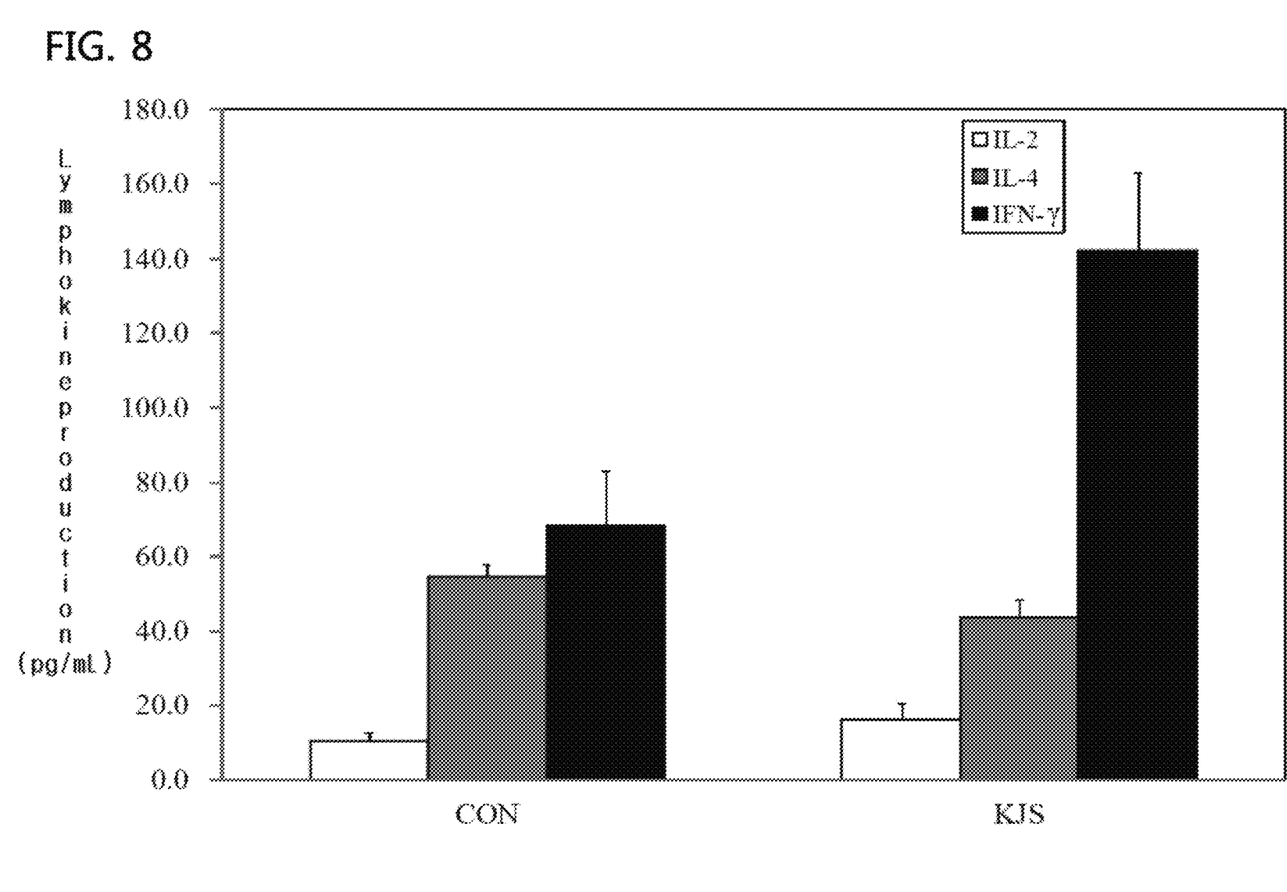

In addition, the effects to the creations of the blood lymphokine (IFN-γ, IL-2, IL-4) are shown in Table 3 and FIG. 8.

TABLE 3

| | Lymphokine production (pg/mL) | | |
|---|---|---|---|
| | IL-2 | IL-4 | IFN-γ |
| CON | 10.7 ± 2.3 | 54.5 ± 3.4 | 68.2 ± 15.1 |
| KJS (250 mg/kg) | 16.4 ± 4.2* | 43.6 ± 4.8 | 142.1 ± 20.8* |

The MS sample (250 mg/kg B.W) was orally administrated for 4 weeks to the BALB/c mouse, and the creation of the blood lymphokine was measured by the ELISA method. As a result, the interferon-γ was increased more than twice, and the IL-2 was increased about 35% as compared with the control group, which proves that as proved in the result of the lymphocyte subpopulation, the activity of the T-lymphocyte was increased, in particular, the creation of the lymphokine like IFN-γ and IL-2 isolated from the Th1 cell was increased. As a result, it is proved that the KJS has an effect of regulating up the immune system activity.

Fourth Embodiment

Antibacterial Activity Characteristic

The experiment was performed with respect to the antibacterial activity characteristics on the sample using the GPP1101B.

The sample was filtered (whatman No. 2) and was frozen and dried, thus obtaining powder. The power was dissolved in sterilized water and was used as the material for experiment.

For the antibacterial evaluation, *pseudomonas aeruginosa, staphylococcus aureus, eschericahia coli, salmonella typhimurium, aspergillus awamori* and FK918 (self-isolated *actinomyces*) were smeared in the growing media by 200 μl and were left alone for 2 hours. The sterilized paper disk (6 mm) was placed, and the sample dissolved in the distilled water of 2 mg/Ml and 4 mg/Ml was divided into 25 ul, and the common bacteria were cultivated for 24 hours at 37° C., and the fungi and *actinomyces* were cultivated for 48~60 hours at 30° C., so the clear zone was measured.

Figure 9:
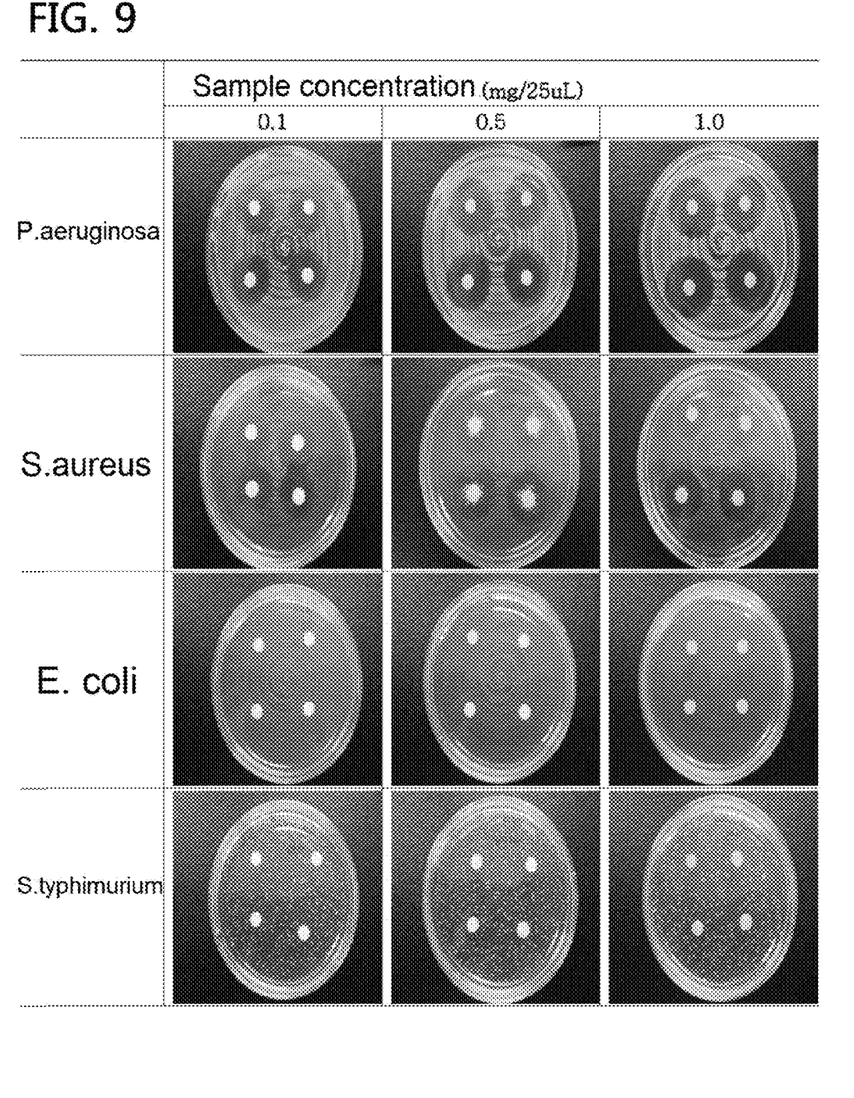
FIGS. 9 and 10 are images illustrating an antibacterial active agent evaluation of preparation according to the present invention.
Figure 10:
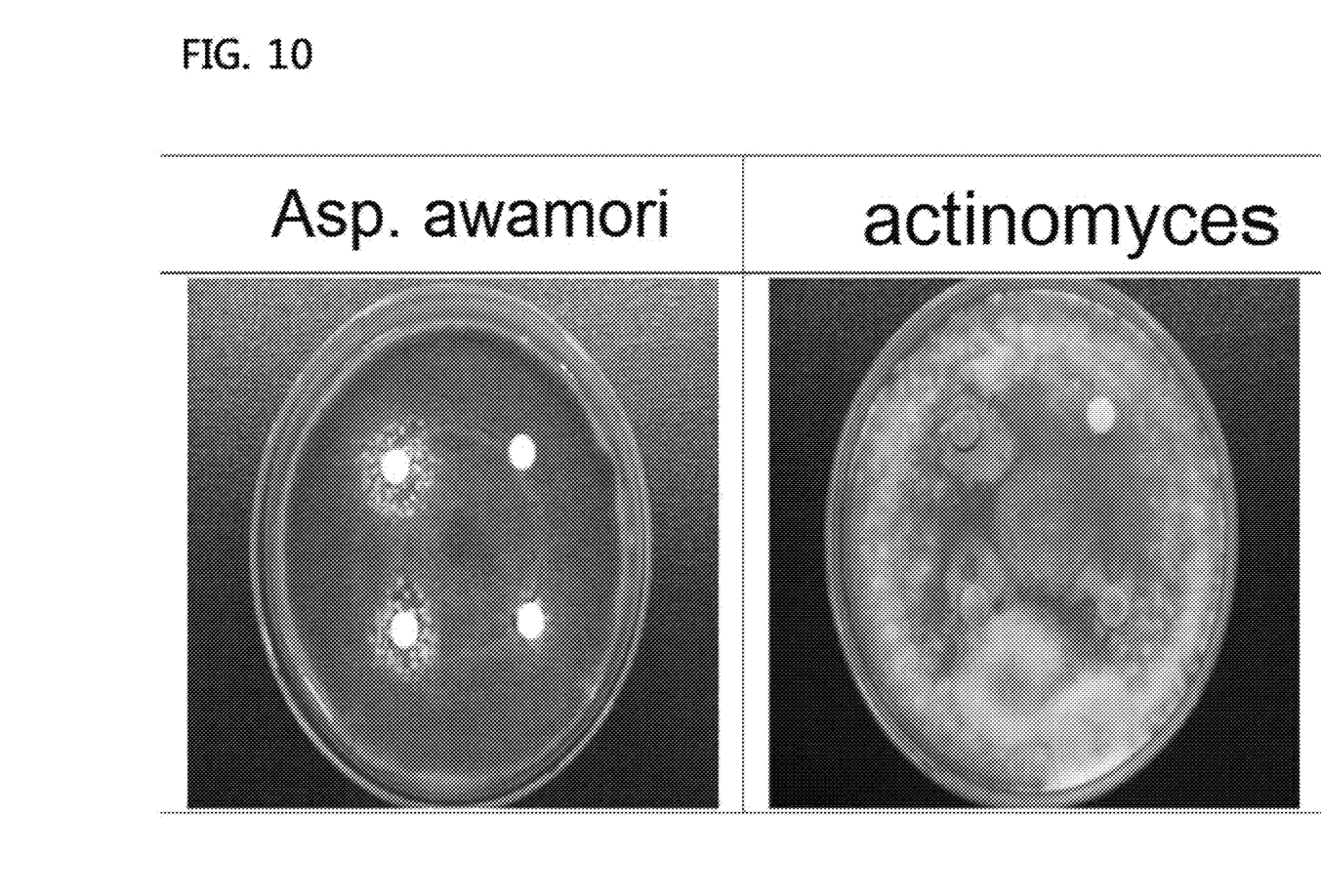

As illustrated in FIGS. 9 and 10, the antibacterial activity with respect to the sample was performed with respect to *staphylococcus aureus* which was added as a gram positive *bacillus* and with respect to *pseudomonas aeruginosa, eschericahia coli, salmonella typhimurium, Asp. awamori* and *actinomyces* (isolated strain in experiment room) which were added as a gram negative *bacillus*.

If the sample concentration was 0.1 mg/25 μl, 0.5 mg/25 μl, 1.0 mg/25 μl, as seen in Table 4, *P. aeruginosa* had the clear zones of 20.79 mm, 23.26 mm, 25.41 mm, and *S. aureus* had the clear zones of 19.73 mm, 19.45 mm, 23.49 mm, but such clear zones were not formed in case of *E. coli S. typhimurium*. In addition, *Asp. awamori* had the clear zones of 9.34 mm, 10.52 mm, 13.94 mm, and *actinomyces* (K918) had the clear zones of 10.67 mm, 9.08 mm, 9.37 mm.

TABLE 4

| strain | Sample concentration (mg/25 ul) | | | |
|---|---|---|---|---|
| | 0.1 | 0.5 | 1.0 | 1.0 (sterilization)[2] |
| P. aeruginosa | 20.79(±1.02) | 23.26(±0.70) | 25.41(±0.46) | — |
| S. aureus | 19.73(±0.88) | 19.45(±1.06) | 23.49(±0.76) | — |
| E. coli | —[1] | — | — | — |
| S. typhimurium | — | — | — | — |
| Asp. awamori | 9.34(±0.25) | 10.52(±0.58) | 13.94(±0.91) | — |
| actinomyces | — | 9.08(±0.37) | 10.67(±0.86) | — |

[1] means that the clear zone was not formed.
[2] means an autoclave at 121° C. for 15 minutes.

As a result of the antibacterial activity evaluation, the sample had strong antibacterial activity against *P. aeruginosa* and *S. aureus* and had low antibacterial activity against *Asp. awamori* and *actinomyces*. However, the sample did not have any bacterial activity against *E. coli* and *S. typhimurium*, and when the sample was processed in the autoclave (121° C., 15 minutes), the antibacterial activity disappeared. Since the antibacterial activity was shown in *P. aeruginosa* which was the gram negative and in *S. aureus* which was the gram positive, it was proved that a specific strain had a unique antibacterial activity.

Fifth Embodiment

Antimutagenic Activity

The experiment was performed with respect to the antimutagenic activity on the sample using the GPP1101B.

The sample was filtered (whatman No. 2) and frozen and dried, so powder was obtained. The power was dissolved in sterilized water, and was used as a material for the experiment.

For the antimutagenic activity evaluation of the sample, the mutation inhibition effects were observed using *S. typhimurium* TA98 strain and the mutagen, for example, 1-nitropyrene, Trp-P-1, aflatoxin B1. Namely, 0.1M sodium phosphate buffer 550 μl, each concentration-based sample of 50 μl and the bacteria culture liquid (1~2×10$^9$ CFU/Ml) 100 μl which was cultivated for 12 hours in Oxoid nutrient broth No. 2 (25 g/l) were mixed in the sterilized experiment tube and were shake-cultivated for 20 minutes at 37° C. and 210 rpm. The culture liquid was diluted with 1/15M phosphate buffer (pH 7.0) and was adjusted to the concentration of 5×10$^3$ CFU/Ml. To the diluted liquid of 100 μl, top agar[agar 6 g, NaCl 5 g per liter (45° C.) 2 Ml were added and mixed and were coated on the plate medium of VBNM[agar 15 g, distilled water 920 Ml, 50×VB salt 20 Ml, 40% glucose 10 Ml, Oxoid nutrient broth No. 2 (25 g/l) 50 Ml] and were cultivated at 37° C. for 12 hours.

The samples were manufactured with the concentrations of 0.1 mg/plate, 0.5 mg/plate, 1.0 mg/plate, thus evaluating antimutagenic activity. As seen in Table 5, in case where mutagen was 1-nitropyrene (1-NP), it was possible to obtain the mutation inhibition effects of 7%, 19%, 54% at each concentration, and in case where the mutagen was Trp-p-1, it was possible to obtain the mutation inhibition effects of 1%, 5%, 9%, and in case where the mutagen was aflatoxin B1 (AFB1), it was possible to obtain the mutation inhibition effects of 10%, 16%, 53%.

TABLE 5

| Mutagen | Inhibition rate (%) | | |
|---|---|---|---|
| | 0.1 mg | 0.5 mg | 1.0 mg |
| 1-NP | 7 | 19 | 54 |
| Trp-p-1 | 1 | 5 | 9 |
| AFB$_1$ | 10 | 16 | 53 |

According to the antimutagenic activity evaluation, the mutagens of 1-NP and AFB1 had high antimutagenic activity of higher than 50% at the concentration of 1.0 mg/plate. According to the anti-bacterial activity evaluation, there was not any antibacterial activity with respect to *S. typhimurium*, so it was proved that the present sample had an antimutagenic activity with respect to 1-NP and AFB1.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

The invention claimed is:

1. A method for manufacturing an immune active agent, the method comprising:
   cultivating a culture liquid by inputting into an extract liquid of *ginseng* or red *ginseng* a strain of *paecilomyces variotii* var. *brunneolus* GPP1101B (microorganism deposit number KCTC 11993BP).

2. The method of claim 1, further comprising filtering over a grown strain to obtain a culture filtrate for use as the culture liquid.

3. The method of claim 1, further comprising freezing, drying, and adding the culture liquid.

4. A method for manufacturing an antibacterial active agent, the method comprising:
   cultivating a culture liquid by inputting into an extract liquid of *ginseng* or red *ginseng* a strain of *paecilomyces variotii* var. *brunneolus* GPP1101B (microorganism deposit number KCTC 11993BP).

5. The method of claim 4, further comprising filtering over a grown strain to obtain a culture filtrate for use as the culture liquid.

6. The method of claim 5, further comprising freezing, drying, and adding the culture liquid.

7. A method for manufacturing an anti-tumor active agent, the method comprising:
cultivating a culture liquid by inputting into an extract liquid of *ginseng* or red *ginseng* a strain of *paecilomyces variotii* var. *brunneolus* GPP1101B (microorganism deposit number KCTC 11993BP).

8. The method of claim 7, further comprising filtering over a grown strain to obtain a culture filtrate for use as the culture liquid.

9. The method of claim 7, further comprising freezing, drying, and adding the culture liquid.

10. A method for manufacturing an anti-mutagen, the method comprising:
cultivating a culture liquid by inputting into an extract liquid of *ginseng* or red *ginseng* a strain of *paecilomyces variotii* var. *brunneolus* GPP1101B (microorganism deposit number KCTC 11993BP).

11. The method of claim 10, further comprising filtering over a grown strain to obtain a culture filtrate for use as the culture liquid.

12. The method of claim 10, further comprising freezing, drying, and adding the culture liquid.

13. A method for manufacturing a culture liquid, the method comprising:
cultivating the culture liquid by inputting into an extract liquid of *ginseng* or red *ginseng* a strain of *paecilomyces variotii* var. *brunneolus* GPP1101B (microorganism deposit number KCTC 11993BP), wherein the strain of *paecilomyces variotii* var. *brunneolus* GPP1101B (microorganism deposit number KCTC 11993BP) is isolated during a *ginseng* fermentation process.

14. The method of claim 13, further comprising obtaining the extract liquid of *ginseng* or red *ginseng* by inputting *ginseng* or red *ginseng* into water heating for 12~72 hours at a temperature of 60~100° C. and filtering the *ginseng* or the red *ginseng* solution.

15. The method of claim 13, further comprising cultivating the extraction liquid of *ginseng* or red *ginseng* into which the strain is contained for 10~60 days at a temperature of 15~35° C. using a cultivator.

16. The method of claim 13, further comprising, after the cultivation is finished, filtering the strain and manufacturing a culture filtrate.

17. A method for preparing a culture filtrate, the method comprising:
heating *ginseng* or red *ginseng* in water for a time period of about 12 to about 72 hours at a temperature of about 60° to about 100° C. to obtain a *ginseng* or red *ginseng* solution;
filtering the *ginseng* or red *ginseng* solution to obtain an extract liquid;
inputting a strain of *paecilomyces variotii* var. *brunneolus* GPP1101B (Microorganism Deposit No. KCTC 11993BP) into the extract liquid to obtain a culture liquid;
cultivating the culture liquid for a time period of about 10 to about 60 days at a temperature of about 15° to about 35° C. using a cultivator to obtain an overgrown strain; and
filtering the overgrown strain to obtain the culture filtrate.

18. The method according to claim 17, further comprising freezing and drying the culture filtrate to obtain a powder.

19. A food product or a medicinal product including the powder prepared by the method according to claim 18.

* * * * *